(12) United States Patent
Michnick

(10) Patent No.: US 6,575,743 B2
(45) Date of Patent: Jun. 10, 2003

(54) DENTAL MIRROR STEM

(75) Inventor: Bruce T. Michnick, Plainview, NY (US)

(73) Assignee: Dentistry Researchers & Designers, Inc, Woodbury, NY (US)

( * ) Notice: Subject to any disclaimer, the term of this patent is extended or adjusted under 35 U.S.C. 154(b) by 7 days.

(21) Appl. No.: 10/050,523

(22) Filed: Jan. 18, 2002

(65) Prior Publication Data

US 2002/0061491 A1 May 23, 2002

Related U.S. Application Data

(63) Continuation of application No. 09/139,092, filed on Aug. 24, 1998, now abandoned.

(51) Int. Cl.[7] ................................................. A61B 1/24
(52) U.S. Cl. ......................................................... 433/30
(58) Field of Search .................. 433/30, 31; 428/912.2; 359/872, 879, 882, 884

(56) References Cited

U.S. PATENT DOCUMENTS

| | | | | |
|---|---|---|---|---|
| 1,504,343 A | * | 8/1924 | Heard ........................ 600/247 |
| 2,525,181 A | * | 10/1950 | Ransdell ..................... 433/30 |
| 2,659,272 A | * | 11/1953 | Goldmann ................... 359/511 |
| 3,031,930 A | * | 5/1962 | Kafig et al. ................. 359/882 |
| 3,755,903 A | * | 9/1973 | Spinello ...................... 433/30 |
| 3,829,199 A | * | 8/1974 | Brown ........................ 359/882 |
| 4,252,522 A | * | 2/1981 | Petty et al. .................. 433/30 |
| 4,512,635 A | * | 4/1985 | Melde ........................ 359/882 |
| 4,605,292 A | * | 8/1986 | McIntosh ................... 359/870 |
| 5,476,194 A | * | 12/1995 | Hippely et al. ............ 222/192 |
| 5,741,132 A | * | 4/1998 | Usui et al. ................... 433/30 |

\* cited by examiner

*Primary Examiner*—Eduardo C. Robert
(74) *Attorney, Agent, or Firm*—Charles I. Bradsky

(57) ABSTRACT

A dental mirror stem in which a shaft abuts against, and is contiguous with a side surface of a substantially circular disc provided with a reflective surface in forming the dental mirror stem with only the shaft supporting the disc as the reflective surface for the mirror, thereby eliminating the frame of prior dental mirror stems in which a glass surface was inserted, to eliminate a channel where tooth particle debris, blood, virus and other contaminants are captured and collected during dental drilling.

11 Claims, 2 Drawing Sheets

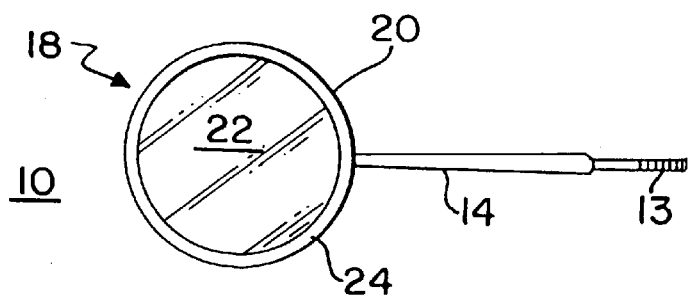
FIG. 1A     PRIOR ART
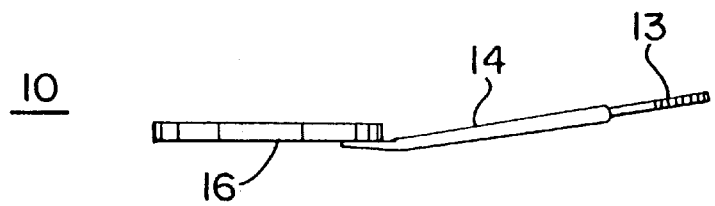
FIG. 1B     PRIOR ART
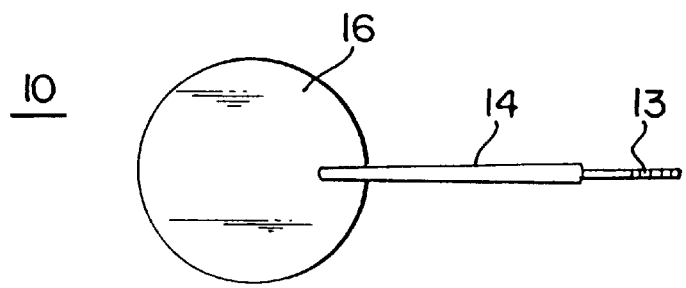
FIG. 1C     PRIOR ART

DENTAL MIRROR STEM (This is in Continuation of application Ser. No. 09/139,092, filed Aug. 24, 1998, now abandoned.)

FIELD OF THE INVENTION

This invention relates to dental mirror stems, in general, and to a new and improved stem for coupling with a handle to provide a mirror used in dentistry, in particular.

BACKGROUND OF THE INVENTION

As is well known and understood, dental mirrors are used extensively in the practice of dentistry, and basically consist of a dental mirror stem (or "mirror portion") attached to a handle, and either by a cone-socket insertion or by a thread joining the two sections. As is also well known, such mirror portion includes a mirrored, reflective surface, within a frame or holder, which together then get coupled with the handle. With the more expensive "front-surface" mirror, the reflected image appears at the "top" of the mirror; with a less expensive "rear-surface" mirror, the reflected image appears at the "bottom" of the mirror.

As is additionally appreciated, the major advantage of the "front-surface" mirror is the much clearer image it presents, as the dentist is not looking through a layer of glass before reaching the reflective surface; with the "rear-surface" mirror, on the other hand, its primary advantages follow from its lower cost, and that it does not scratch as easily.

More-and-more in the practice of dentistry, today, air-abrasive technology is being employed to drill very fine preparations on teeth. Experience has shown, however, that the particles of teeth thus dislodged, along with the particles of aluminum oxide wearing off the dental drill, fly about the mouth, striking the glass mirror—and to the extent that the surface etching which results (particularly at high pressure and speed) oftentimes so deteriorates the reflected image as to make the mirror essentially unusable. Nevertheless, the advantage of this new technology continues to extend into the profession, and chiefly because the resultant air-blasting produces substantially no micro-cracks in the dental enamel, because its method of operation is much less painless than associated with the previously employed dental drill, and because its careful use can allow extremely fine openings to be made in the tooth to check to see if there is any decay present.

One type of solution that has been proposed to protect the glass mirror surface is to temporarily lie over it a plastic substrate which itself incorporates a light reflective surface. Then, whether the dental mirror be fabricated of fibercore material to allow its use in electrosurgery without being electrically conductive, or whether the mirror is used of a metal fabrication sufficiently strong to exert pressure in retracting the cheek and tongue, it is the plastic substrate that gets damaged by the debris flying about the mouth, and not the glass surface to which the plastic substrate is secured. After the coarse drilling with the air-abrasive apparatus is finished, the plastic substrate is merely pulled away, and the clearer producing image of the glass surface alone is employed for allowing the dentist to inspect the work done and to complete the procedure.

While these types of "disposable mirror surfaces" serve their purpose adequately well in this environment, analysis has shown that a problem continues to exist. In particular, for example, the glass reflecting surface is positioned within a frame or holder of the mirror stem, leaving a surrounding channel between the side edge of the glass mirror and the wall of the frame in defining the diameter of the mirror and in establishing the configuration of the reflective surface. Testing has shown that no matter how much the dental mirror may be disinfected, or sterilized in an autoclave, the debris flying about the mouth that gets captured in this channel, stays and collects there. Even though the rim area defined by the side wall of the frame is quite fine, analysis has shown that there continues to be retained in the channel remnants of the grinding debris, elements of the patient's own tissue cells, bacteria and other organisms. A consideration of these circumstances illustrates the existence of a possible hygienic problem area which it would be desirable to eliminate.

OBJECTS OF THE PRESENT INVENTION

It is an object of the present invention, therefore, to provide a new and improved dental mirror which is characterized by the absence of this channel surrounding the mirror-reflective surface.

It is an object of the invention, also, to provide such a mirror which continues to be able to accept the temporary securement of these plastic substrates in protecting the glass mirror during the coarse grinding actions of dental treatment—whether the mirror be of the "front-surface" or "rear-surface" variety.

It is another object of the invention to eliminate this debris-capturing channel, while, at the same time, permitting the plastic reflective surface to be temporarily securable on either or both of the upper and lower surfaces of the frame in which the glass mirror is inserted, to assist the dentist in the treatment of the patient.

It is yet another object of the invention to eliminate these debris-capturing and collecting channels, whether the resulting mirror be provided with a threaded end for joining the dental mirror stem to its handle, whether the join between the two be of an otherwise cone-socket arrangement, whether the combination so formed be used as a "front-surface" or "rear-surface" mirror, and regardless of whether the mirror be formed of the more typical metal handle composition, or whether it be of a plastic material for use in electrosurgery.

SUMMARY OF THE INVENTION

As will become clear from the following description, these objectives are attained through the invention of a dental mirror stem including a shaft having first and second ends, and a substantially circular disc having flat upper and lower surfaces extending to a side surface of the disc in defining the diameter of the disc and in establishing the configuration of the disc as being substantially and continuously flat. Means are then provided to secure the first end of the shaft to the disc, and with a plastic substrate having a reflective surface then secured to at least one of the upper and lower surfaces of the disc. In this manner, the previous side wall of the prior art frame defining the channel is eliminated; also, the probability of tooth particle damage to a glass mirror surface as the dislodged tooth particles fly about is obviated by the use of the plastic substrate. As will become more particularly clear, by having a substantially circular disc without the channel formed in the frame or holder where the reflective surface seats, the capture and collection of the grinding debris is thereby avoided.

In a preferred embodiment of the invention to be described, the shaft of the dental mirror stem secures to a side surface of the substantially circular disc, so as to permit plastic substrates to be temporarily secured, as by an adhesive coupling, to either or both of the upper and lower surfaces of the disc. As will be appreciated, such construction permits the shaft and substantially circular disc to be formed by a metal stamping process—whether, or not, the handle of the mirror is similarly so formed. In a further embodiment of the invention, the shaft is bent around to the lower surface of the substantially circular disc to be secured there, in a manner akin to the dental mirror stem used in the prior art. In either event, however, the capturing channel for debris present in designs of the type utilized today will be seen to be eliminated.

In other words, the dental mirror stem with the substrate attached is used where the coarse drilling is to take place, with the attendant debris, tissue cells, bacteria, etc. being present, but without any channel being there to capture them. After that is completed, the conventional "front" or "rear" surface mirror is employed for the fine finishing of the dental treatment, without fear of extensively damaging the mirror surface. The substrate of the dental mirror stem is peeled away, the stem is sterilized in any appropriate manner, and a new substrate attached for the next patient usage; however, no collected material is retained for transmittal to that next patient.

BRIEF DESCRIPTION OF THE DRAWINGS

These and other features of the present invention will be more clearly understood from a consideration of the following description, taken in connection with the accompanying drawing, in which:

FIGS. 1A, 1B and 1C are top, side and bottom views of a dental mirror stem of the type characterizing the prior art;

DETAILED DESCRIPTION OF THE DRAWINGS

Figure 3:
FIG. 3 depicts a standard handle which may be incorporated with the dental mirror stems of FIGS. 1 and 2.

In FIGS. 1A–C, the dental mirror stem 10 couples with the handle 12 of FIG. 3 by means of its screw threads 13, although a cone-socket coupling can be employed as well. The stem 10 includes a shaft 14 secured to the underside 16 of a metal frame or holder 18, as by welding. The frame 18 includes a surrounding side wall 20 which receives a glass mirror 22 of either front surface or rear surface type. As shown in FIG. 1A, the glass mirror 22 sits wholly within the surrounding side wall 20, but with a channel 24 separating the two, in accordance with usual manufacturing processes. As previously mentioned, it is within the channel 24 that the ground tooth debris, the abrasives, and the aluminum oxide particles from the drill bit are captured and collected during the dental drilling process. Testing has shown that even though this debris, abrasives, and aluminum oxide particles are thereafter sterilized along with the handle in an autoclave, for example, the channel 24 cannot readily be cleaned out, with the result being that the captured and collected material is transferred from patient-to-patient. With the dental mirror stem of the invention, on the other hand, such channel 24 is eliminated, so no capture or collection of debris, abrasives, and aluminum oxide particles occurs.

As will be seen from the following description, the teachings of the invention are particularly attractive in those continuing instances where the procedures employed by the dentist in drilling lead to occasions where the surface of the glass mirror employed is susceptible to scratching by the tooth debris and the abrasives flying about the mouth during the dental drilling process.

Figure 2A:
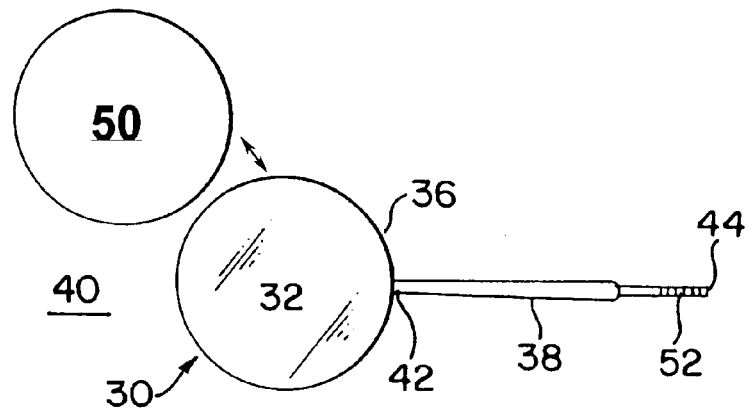
FIGS. 2A, 2B and 2C are top, side and bottom views of a dental mirror stem embodying the invention.
Figure 2B:
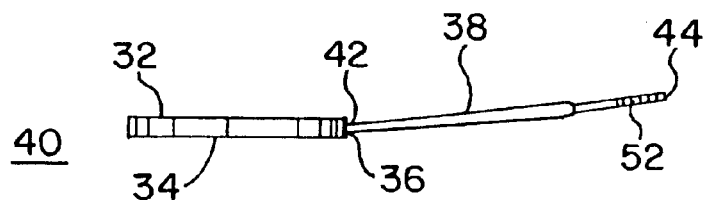
Figure 2C:
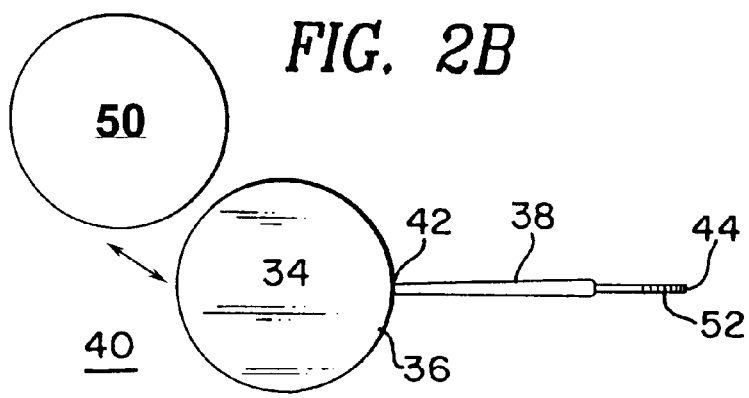

Thus, and as shown in FIGS. 2A–C, the frame 18—with its surrounding side wall 20 and its glass mirror 22—are replaced by a substantially circular disc 30 having flat upper and lower surfaces 32, 34 extending to a side surface 36 in defining the diameter of the disc 30 and in establishing its configuration as substantially and continuously flat. The shaft 38 of the dental mirror stem 40 may be secured in any appropriate manner to the side surface 36 as shown, or to the lower surface 34. Such securement is with a first end 42 of the shaft 38, its second opposite end 44 being joined with the handle 12 of FIG. 3 in any usable way—for example, by threading or by cone-socket insertion.

In accordance with the invention, a plastic substrate 50 having a reflective surface is secured to at least one of the upper and lower surfaces 32, 34 of the substantially circular disc 30, extending to the side surface 36. Being of Mylar, or any other material that will provide an adequate image and which is relatively inexpensive, such substrate is intended to be temporarily secured, as by adhesive, to either or both of the surfaces 32, 34, and is preferably configured to be substantially circular in placement over the disc 30. With the substantially circular disc 30 and the shaft 38 being fabricated of a metal composition, for example, the dental mirror that results will have sufficient strength and rigidity to retract the cheek and tongue by virtue of the pressure imparted in use by the dentist. Whether the disc 30 and the shaft 38 are fabricated of a stainless steel material, as is typically desirable, or where they are composed of a fibercore material for use in electrosurgery, on the other hand, the advantages that they offer will be understood—as the dental debris, the abrasives, and the drill bit particles fly about the mouth while the dental drilling is ongoing.

Once the coarse drilling with the air-abrasive particles is no longer needed, the dental mirror stem 40 may be disconnected from the handle 12, by an unscrewing where such threads as 52 are employed, for sterilization in any appropriate, with the handle 12 then being re-connected with the conventional, prior art dental mirror stem, of either "front-surface" or "rear-surface" type, in completing the dental procedure. Alternatively, a separate combination of handle and such dental mirror stem could be employed, but with the results being that the pitting, and damage done to the reflective surface, is done to that of the plastic substrate 50, and not to any mirror surface. Once the substrate 50 is peeled away from the disc 30, that substrate is then discarded, the disc is sterilized, and a new plastic substrate replaced in position on the disc 30 for later use. With the substrate 50 thus extending to the side surface of the substantially circular disc 30, in this manner—and with the disc 30 being substantially and continuously flat across its face—no channel will be seen to be present, as contrasted with the dental mirror stems of the prior art, to capture and collect the abrasives, grinding debris, tissue cells, bacteria, etc. produced during the drilling process.

While there has been described what is considered to be a preferred embodiment of the present invention, it will be readily appreciated by those skilled in the art that modifications can be made without departing from the scope of the teachings herein. For example, although the dental mirror stem of the invention has been illustrated as being one where the shaft 38 is secured to the side surface 36 of the disc 30, the advantages of the invention would follow equally as well where the shaft 38 were to couple to the underside 34 of the disc 30, in a manner comparable to that of FIG. 1B. Obviously, such placement might interfere with those instances of use where it is desired to place the substrate 50 at the lower surface 34 of the disc 30, as well as at the upper surface 32, especially in those instances where the dentist might find it useful to have the protective reflective surface on both sides of the disc employed. Similarly, although the mirror stem has been specifically described as being of a metal or stainless steel composition, it will be appreciated that such enables a manufacture to take place by a metal stamping process; where that is not desired, the mirror stem could be composed of a plastic material. In either event, the disc and the shaft would preferably be manufactured at the same time, of the same material. For at least such reasons, therefore, resort should be had to the claims appended hereto for a true understanding of the scope of the invention.

I claim:

1. A dental mirror stem to be coupled to a handle during a coarse, debris-producing dental drilling procedure, comprising:

a substantially circular disc having flat upper and lower surfaces extending to a side surface of said disc in defining a diameter of said disc and in establishing a configuration of said disc as substantially and continuously flat throughout and across;

a shaft having a first end abutting against and contiguous with said side surface of said substantially circular disc, and also having a second end;

and a plastic substrate adhesively secured to at least one of said upper and lower surfaces of said disc during said coarse dental drilling procedure in forming the dental mirror stem;

with only said shaft supporting said continuously flat disc and said plastic substrate, and with said substrate serving as the only reflective surface for said mirror stem;

and with said disc and said shaft being of a composition to withstand dental sterilization after peeling away of the plastic substrate used in the coarse dental drilling procedure and prior to the replacement with a new adhesively secured plastic substrate.

2. The dental mirror stem of claim 1 including a pair of plastic substrates adhesively secured to respective ones of said upper and lower surfaces of said disc.

3. The dental mirror stem of claim 2 in combination with a handle coupled to said second end of said shaft during said coarse dental drilling procedure.

4. The dental mirror stem of claim 1 in combination with a handle coupled to said second end of said shaft during said coarse dental drilling procedure.

5. The dental mirror stem of claim 1 wherein said second end of said shaft is threaded.

6. The dental mirror stem of claim 1 in which said shaft and said substantially circular disc are fabricated of a metal composition.

7. The dental mirror stem of claim 6 wherein said shaft and said substantially circular disc are formed by a metal stamping process in which said first end of said shaft and said side surface of said substantially circular disc are coupled together.

8. The dental mirror stem of claim 1 wherein said shaft and said substantially circular disc are fabricated of a stainless steel material.

9. The dental mirror stem of claim 1 wherein said shaft and said substantially circular disc are each composed of a plastic material.

10. The dental mirror stem of claim 9 wherein said shaft and said substantially circular disc are each composed of a fibercore material.

11. A combination for use in a dental drilling procedure comprising:

a dental mirror handle adapted for coupling to the shaft of a dental mirror stem; and a pair of dental mirror stems serially coupled in use to said handle, the first of said dental mirror stems to be coupled to said handle in use in coarse dental drilling and the second of said dental mirror stems to be coupled to said handle in use after coarse dental drilling is completed, said first dental mirror stem including:

a substantially circular disc having flat upper and lower surfaces extending to a side surface of said disc in defining a diameter of said disc and in establishing a configuration of said disc as substantially and continuously flat throughout and across;

a shaft having a first end abutting against and contiguous with said side surface of said substantially circular disc, and also having a second end;

and a plastic substrate adhesively secured to at least one of said upper and lower surfaces of said disc during said coarse dental drilling procedure in forming the dental mirror stem;

with only said shaft supporting said continuously flat disc and said plastic substrate, and with said substrate serving as the only reflective surface for said mirror stem;

and with said disc and said shaft being of a composition to withstand dental sterilization after peeling away of the plastic substrate used in the coarse dental drilling procedure and prior to the replacement with a new adhesively secured plastic substrate;

and said second dental mirror stem including:

a frame having a surrounding side wall;

a shaft having a first end secured to said frame and a second end to couple to said dental mirror handle; and a glass mirror within said surrounding side wall of said frame.

\* \* \* \* \*